United States Patent [19]

Appel et al.

[11] 4,370,276
[45] Jan. 25, 1983

[54] PROCESS FOR THE CONTINUOUS PREPARATION OF DIALKYLPEROXYDICARBONATES

[75] Inventors: Hans Appel; Gottfried Brossmann, both of Munich, Fed. Rep. of Germany

[73] Assignee: Peroxide Chemie GmbH, Munich, Fed. Rep. of Germany

[21] Appl. No.: 302,863

[22] Filed: Sep. 16, 1981

[30] Foreign Application Priority Data

Oct. 9, 1980 [DE] Fed. Rep. of Germany ....... 3038164

[51] Int. Cl.³ .......................................... C07C 179/18
[52] U.S. Cl. .................................................. 260/463
[58] Field of Search ........................................ 260/463

[56] References Cited

U.S. PATENT DOCUMENTS 3,499,919 3/1970 Gerritsen et al. ................... 260/463
3,657,312 4/1972 D'Angelo ............................ 260/463
3,950,375 4/1976 McKee et al. ...................... 260/463

FOREIGN PATENT DOCUMENTS 1259325 1/1968 Fed. Rep. of Germany ...... 260/463
1265154 4/1968 Fed. Rep. of Germany .
108272 9/1974 Fed. Rep. of Germany .

OTHER PUBLICATIONS

German Patent Abstracts, Abstract of Fed'l. Rep. Germany Patent Specification 1,265,154, vol. 8, No. 19.

*Primary Examiner*—Donald G. Daus
*Assistant Examiner*—M. C. Eakin
*Attorney, Agent, or Firm*—Felfe & Lynch

[57] ABSTRACT

The present invention provides a process for the continuous production of dialkylperoxydicarbonates of the general formula:

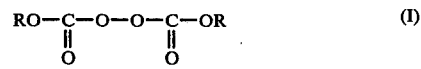

in which R stands for the same or different, straight-chained, cyclic or branched alkyl radicals containing 6 to 18 carbon atoms, by the continuous reaction of a chloroformic acid ester of the general formula:

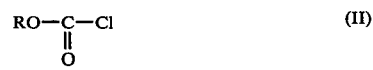

wherein R has the above-given meanings, in an aqueous medium with hydrogen peroxide and an alkali metal hydroxide at a temperature of from $-10°$ C. to $+50°$ C. in at least two reaction zones connected in series and continuous isolation of the dialkylperoxydicarbonate formed from the solvent-free reaction mixture with the use of a centrifuge, wherein the reaction is carried out in the presence of a surfactant and the dialkylperoxydicarbonate formed is separated in molten form from the alkaline reaction mixture heated to or just above the melting temperature of the dialkylperoxydicarbonate.

14 Claims, No Drawings

PROCESS FOR THE CONTINUOUS PREPARATION OF DIALKYLPEROXYDICARBONATES

This invention relates to a process for the production of dialkylperoxydicarbonates.

More specifically the invention relates to production of dialkylperoxydicarbonates of the general formula $$RO-\underset{\underset{O}{\|}}{C}-O-O-\underset{\underset{O}{\|}}{C}-OR \qquad (I)$$

in which R stands for the same or different, straight-chained, cyclic or branched alkyl radicals containing 6 to 8 carbon atoms, and especially for the continuous production of dimyristylperoxydicarbonate and dicetylperoxydicarbonate, by the continuous reaction of a chloroformic acid ester of the general formula:

$$RO-\underset{\underset{O}{\|}}{C}-Cl \qquad (II)$$

wherein R has the above-given meaning and is preferably a myristyl or the cetyl radical, in an aqueous medium with hydrogen peroxide and an alkali metal hydroxide at a temperature of from $-10°$ C. to $+50°$ C. in at least two reaction zones connected in series and continuous isolation of the dialkylperoxydicarbonate formed from the solvent-free reaction mixture with the use of a centrifuge.

The continuous production of dialkylperoxydicarbonates has been known for a long time. Thus, Federal Republic of Germany Patent Specifications Nos. 12 65 154 and 12 59 325 disclose such processes in which the reaction of the reaction components, namely of the chloroformic acid ester, hydrogen peroxide and alkali metal hydroxide, takes place in an aqueous medium and the reaction products are taken up in an organic solvent. These processes are not satisfactory, especially because of the organic solvents and especially of the halogen-containing organic solvents used.

German Democratic Republic Patent Specification No. 108,272 describes a process for the continuous production of dialkylperoxydicarbonates by the reaction of chloroformic acid esters with hydrogen peroxide in the presence of alkali metal hydroxides which is also preferably carried out in the presence of a reaction-inert solvent.

Finally, U.S. Pat. No. 3,950,375 describes the initially mentioned solvent-free process for the continuous production of dialkylperoxydicarbonates, the separation of the solid dialkylperoxydicarbonates from the reaction mixture hereby takes place with the use of a liquid-solid centrifuge.

It is an object of the present invention to provide a continuously operating process for the production of, in particular, solid dialkylperoxydicarbonates, which gives a high yield, referred to the chloroformic acid esters used, gives dialkyperoxydicarbonates with high purity, gives a low environmental contamination and provides a uniform product of high quality, obtained in dry form.

Thus, according to the present invention, there is provided a process for the continuous production of dialkylperoxydicarbonates of the general formula:

$$RO-\underset{\underset{O}{\|}}{C}-O-O-\underset{\underset{O}{\|}}{C}-OR \qquad (I)$$

in which R stands for the same or different, straight-chained, cyclic or branched alkyl radicals containing 6 to 18 carbon atoms, by the continuous reaction of a chloroformic acid ester of the general formula:

$$RO-\underset{\underset{O}{\|}}{C}-Cl \qquad (II)$$

wherein R has the above-given meanings, in an aqueous medium with hydrogen peroxide and an alkali metal hydroxide at a temperature of from $-10°$ C. to $+50°$ C. in at least two reaction zones connected in series and continuous isolation of the dialkylperoxydicarbonate formed from the solvent-free reaction mixture with the use of a centrifuge, wherein the reaction is carried out in the presence of a surfactant and the dialkylperoxydicarbonate formed is separated in molten form from the alkaline reaction mixture heated to or just above the melting temperature of the dialkylperoxydicarbonate.

In carrying out the process according to the present invention the chloroformic acid ester of general formula (II) used as starting material is preferably employed in the purest possible form, chloroformates with a purity of 96 to 98% or possibly more being especially preferred.

The hydrogen peroxide used for carrying out the process according to the present invention is preferably employed in 70% form and is preferably supplied to the reaction mixture in an excess of 10 to 60% over the stoichiometrically necessary amount. According to a preferred embodiment of the process according to the present invention for the production of dimyristylperoxydicarbonate or of dicetylperoxydicarbonate, the hydrogen peroxide is preferably used in a stoichiometric excess of about 28% or about 54%, respectively.

The alkali metal hydroxide used in the process according to the present invention is preferably employed in an excess of 5 to 30% and more preferably of 5 to 20% over the stoichiometrically necessary amount. The alkali metal hydroxide used is preferably sodium hyroxide but potassium hydroxide can also be used. According to a preferred embodiment of the process, the alkali metal hydroxide is added to the reaction zone in such an amount that the reaction mixture emerging from the reaction zone has a pH value of 10 to 12.5 and preferably of 11 to 12. Too high a pH value results in losses of yield, whereas a pH value lying below the lower limiting value results in higher chlorine values.

An important feature of the process according to the present invention is that it is carried out in the presence of a surfactant. For this purpose, use can be made of any desired surfactant which does not disturb the course of the reaction. However, anion-active agents, for example sulphosuccinic acid esters and sodium alkylpolyglycol ether phosphates or the mixtures of two or more of these surfactant have proved to be especially suitable.

According to the present invention, the surfactant may be used in an amount of 0.8 to 2.5 g. and preferably of 1.1 to 1.8 g., referred to 100 g. of the chloroformic acid ester employed.

The use, according to the process of the present invention, of a surfactant leads not only to an improved and more constant reaction but, surprisingly, also results in higher active oxygen values in the end product obtained.

The reaction can be accelerated by adding a ditert.-alkylacetyleneglycol to the surfactant.

It is preferable to operate at a reaction temperature of from 15° to 35° C. and more preferably of from 20° C. to 30° C. and to carry out the reaction in such a manner, i.e. with the use of two reaction zones connected one behind the other, that a residence time or a reaction time is obtained of 30 to 60 and preferably of 40 to 50 minutes.

After the reaction, an aqueous reaction mixture is obtained in which the dialkylperoxydicarbonate is present in suspended form.

In order to isolate the product, the aqueous alkaline reaction mixture is heated as quickly as possible, i.e. in the smallest possible beating vessel or in a in line mixer by the addition of hot water or steam, to a temperature which corresponds to the melting temperature of the dialkylperoxydicarbonate or some degrees higher i.e. at most about 5° C. thereover. Subsequently, the molten dialkylperoxydicarbonate is separated from the aqueous, alkaline reaction mixture with the use of a continuously operating liquid-liquid centrifuge. For this purpose, it is advantageous to use a disc type separator in which the phase separation can be achieved very quickly and in a gentle manner.

It has proved to be of advantage to add to the reaction mixture obtained or to the dialkylperoxydicarbonate melt formed about 0.02 to 0.1% and preferably about 0.06% of pyridine, referred to the isolated dialkylperoxydicarbonate, since, surprisingly, it is hereby possible to prevent the static charging of the product in flake form.

After the separation of the liquid-liquid centrifuge, the dialkylperoxydicarbonate melt is converted into flakes on a flaking roller.

For carrying out the process according to the present invention, the reaction vessel used is preferably a stirred vessel equipped with a cooling jacket into which vessel the starting materials used can be introduced via an immersion tube. This immersion tube preferably comprises two concentrically arranged tubes, the chloroformic acid ester being introduced via the inner tube and the aqueous components via the concentrically arranged outer tube, which is preferably somewhat longer than the inner tube.

With the help of intermediate plates, the content of the reactor can be divided into two or more reaction zones, a stirrer propeller being provided in each zone. Furthermore, a separating disc can be provided below the overflow tube as a protection against spraying and for damping stirrer pulsations.

Since the reaction of the chloroformic acid ester with hydrogen peroxide is very sluggish and a reaction time of 30 to 60 minutes is necessary, two such stirred vessel are preferably arranged in series, the second stirred vessel being equipped in the same way as the first one. The overflow from the first vessel to the second vessel can take place via the immersion tube in the lower chamber of the second stirred vessel.

The most favourable reaction temperature has been found to be 15° to 35° C. and especially 30° C. in the first stirred vessel and 20° to 35° C. and especially 25° C. in the second stirred vessel. In the case of the selected residence time, lower temperatures give higher chlorine values. A prolongation of the reaction time or of the residence time over 60 and especially 50 minutes is not desirable since the amount of reaction mixture is thereby increased. On the other hand, a higher temperature is unsuitable because of the low stability of the alkaline hydrogen peroxide solution.

The dialkylperoxydicarbonate formed is isolated in a molten state from the alkaline reaction mixture as it emerges from the second stirred vessel. In a molten state, the solid dialkylperoxydicarbonates behave similarly to fatty acid diacyl peroxides, i.e. they decompose very quickly. However, the dialkylperoxydicarbonates are substantially more unstable, for which reason, for example, washing is not possible after the separation of the mother liquor. This high instability of the melt requires the shortest possible residence time of the dialkylperoxydicarbonate in the molten state and a very careful separation of the melt from the mother liquor. According to the present invention, this is achieved by the alkaline separation with the use of a liquid-liquid centrifuge, an emulsion effect thereby clearly occurring, which favours the formation of a purer product.

After leaving the second stirred reactor, the reaction mixture is passed into a small melting vessel (stirrer vessel with heating jacket) in which, by the supply of warm water and steam, the melt temperature of the dialkylperoxydicarbonate is adjusted (which, in the case of the preferably produced dimyristylperoxydicarbonate and dicetylperoxydicarbonate, is 46° and 56° C., respectively). Because of the critical residence time, the vessel must be as small as possible. The use of a in line heater or static mixer is also possible. For the phase separation, the mixture obtained is preferably supplied to a disc type separator.

The construction of the disc separator is of importance, the use of a separator with a free outlet of the light phase being advantageous. In addition, the flow-off plate in the cover of the separator should be of double-walled construction in order thus to control temperature of the melt.

As a final step, the percarbonate melt is converted into flakes on a flaking roller. The product solidifies very quickly on the flaking roller to give flakes, the size of which can be controlled via the cooling of the roller. The proportion of dust obtained is small. It is interesting that, according to a preferred embodiment of the process of the present invention, it is possible to prevent static charging of the flakes by the addition to the reaction mixture of 0.02 to 0.1% and preferably of 0.06% of pyridine, referred to the isolated dialkylperoxydicarbonate.

In comparison with the above-discussed prior art processes, the process according to the present invention has considerable advantages insofar as the process is very simple to carry out, gives a product of high purity in high yield, even when using impure starting materials, and only very little organic material passes into the waste water.

The following Examples are given for the purpose of illustrating the present invention:

EXAMPLE 1

An open stirred vessel, equipped with a high speed stirrer and an overflow tube, is supplied, per minute, with 135 ml. myristyl chloroformate, 65 ml 7.8 N aqueous sodium hydroxide solution, 11 ml. hydrogen peroxide (70 wt.%), 1.5 ml. of a surfactant solution and 700 ml. of demineralised water, the reaction temperature being kept at about 30° C. by cooling with water. The reaction components are introduced through immersion tubes which end just above the bottom of the reactor. The reaction mixture flowing off through the overflow is, for completing the reaction, passed into a second stirred vessel where a temperature of about 25° C. is maintained by cooling. The size of the stirrer vessels is so chosen that the average residence time is about 50 minutes.

The suspension flowing off from the second stirred vessel is heated to 46° C. by the addition of about 600 ml./min. of demineralised water with a temperature of 80° C., the dimyristylperoxydicarbonate thereby being melted. Controlling the temperature to 46° C. as precisely as possible is important and can be achieved by the precisely controlled addition of the hot water. The reaction suspension can be mixed with the hot water in a in line mixer or possibly in a small stirrer vessel.

In a subsequently connected disc type separator, the dimyristylperoxydicarbonate melt is then separated from the aqueous phase. The melt coming from the separator is passed by the shortest possible route to a flaking roller, where it solidifies and can be removed in the form of flakes.

In this way, 116 g./minute of dimyristylperoxydicarbonate are obtained with a peroxide content of 97%, which corresponds to a content of active oxygen of 3.01%. This corresponds to a yield of 97.3% of theory, referred to the myristyl chloroformate employed. The analysis of the product shows a chlorine content of about 0.06%.

EXAMPLE 2

The procedure of Example 1 is repeated except that the stirrer vessel is supplied, per minute, with 135 ml. cetyl chloroformate, 60 ml. 7.8 N aqueous sodium hydroxide solution, 12 ml. 70 wt.% hydrogen peroxide, 1.8 ml. of a surfactant solution and 930 ml. demineralised water.

The melt temperature is adjusted to 56° C. by adding about 1000 ml./minute of demineralised water with a temperature of 90° C.

After cooling the material in flake form on the flaking roller, 115 g./minute of dicetylperoxydicarbonate are obtained with a peroxide content of 97%, corresponding to 2.72% of active oxygen, which corresponds to a yield of 97.4% of theory, referred to the chloroformate employed.

It will be understood that the specification and examples are illustrative but not limitative of the present invention and that other embodiments within the spirit and scope for the invention will suggest themselves to those skilled in the art.

What is claimed is:

1. Process for the continuous production of dialkylperoxydicarbonates of the formula

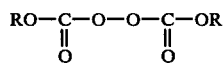

(I)

in which R is individually selected from straight-chained, cyclic or branched alkyl radicals of 6 to 18 carbon atoms, which process comprises continuously reacting a chloroformic acid ester of the formula

(II)

wherein R is identified as above, in an aqueous medium with hydrogen peroxide and an alkali metal hydroxide at a temperature of from −10° C. to +50° C. in at least two reaction zones connected in series, continuously isolating the dialkylperoxydicarbonate formed from the solvent-free reaction mixture with the use of a centrifuge, wherein the reaction is carried out in the presence of a surfactant and the dialkylperoxydicarbonate formed is separated in molten form from the alkaline reaction mixture heated to or just above the melting temperature of the dialkylperoxydicarbonate.

2. Process as claimed in claim 1, wherein the reaction is carried out with the use of an excess of hydrogen peroxide of 10 to 60% over the stoichiometrically necessary amount.

3. Process as claimed in claim 1, wherein the reaction is carried out with the use of an alkali metal hydroxide excess of 5 to 30% over the stoichiometrically necessary amount.

4. Process as claimed in claim 1, wherein the alkali metal hydroxide is introduced into the reaction zone in an amount such that the reaction mixture emerging from the reaction zone has a pH value of 10 to 12.5.

5. Process as claimed in claim 4, wherein the alkali metal hydroxide is introduced into the reaction zone in an amount such that the reaction mixture emerging from the reaction zone has a pH value of 11 to 12.

6. Process as claimed in claim 1, wherein the reaction is carried out with the use of a reaction time of 30 to 60 minutes.

7. Process as claimed in claim 1, wherein an anion-active surfactant is used.

8. Process as claimed in claim 7, wherein a sulphosuccinic acid ester, a sodium alkylpolyglycol ether phosphate or a mixture of two or more of these surfactants is used.

9. Process as claimed in claim 1, wherein, for the acceleration of the reaction, a di-tert.-alklacetyleneglycol is added to the surfactant.

10. Process as claimed in claim 1, wherein the surfactant is used in an amount of 0.08 to 2.5 g. of surfactant per 100 g. of chloroformic acid ester used.

11. Process as claimed in claim 1, wherein the dialkylperoxydicarbonate is isolated with the use of a continuously operated liquid-liquid centrifuge.

12. Process as claimed in claim 11, wherein a disc type separator is used as the liquid-liquid centrifuge.

13. Process as claimed in claim 1, wherein about 0.02 to 0.1% of pyridine, referred to the isolated dialkylperoxydicarbonate is added to the reaction mixture or to the dialkylperoxydicarbonate.

14. Process as claimed in claim 1, wherein the separated dialkylperoxydicarbonate melt is flaked on a flaking roller.

* * * * *